(12) United States Patent
Lee et al.

(10) Patent No.: US 8,287,707 B2
(45) Date of Patent: Oct. 16, 2012

(54) DEVICE FOR CONTROLLING PARTICLE DISTRIBUTION IN AN EVAPORATING DROPLET USING RADIAL ELECTROOSMOTIC FLOW

(75) Inventors: Jeong-gun Lee, Seoul (KR); Sung-jae Kim, Pohang-si (KR)

(73) Assignee: Samsung Electronics Co., Ltd. (KR)

( * ) Notice: Subject to any disclaimer, the term of this patent is extended or adjusted under 35 U.S.C. 154(b) by 1218 days.

(21) Appl. No.: 11/501,124

(22) Filed: Aug. 8, 2006

(65) Prior Publication Data
US 2007/0170058 A1    Jul. 26, 2007

(30) Foreign Application Priority Data

Jan. 26, 2006    (KR) .................. 10-2006-0008237

(51) Int. Cl.
*B01D 57/00* (2006.01)
*B01D 15/00* (2006.01)
(52) U.S. Cl. ........ 204/450; 204/453; 204/547; 422/105; 210/198.2
(58) Field of Classification Search .................. 204/450, 204/453, 547; 422/105; 210/198.2
See application file for complete search history.

(56) References Cited

U.S. PATENT DOCUMENTS

| RE34,806 E | * | 12/1994 | Cann | ............................. | 427/446 |
| 2002/0092366 A1 | * | 7/2002 | Brock et al. | ................ | 73/863.32 |
| 2004/0136876 A1 | * | 7/2004 | Fouillet et al. | ................ | 422/100 |

OTHER PUBLICATIONS

Kim Y.; Hurst, G.B.; Doktycz, M.J.; Buchanan, M.V.; Anal. Chem 2001, vol. 73, pp. 2617-2624.
Westman, A.; Demirev, P.; Huth-Fehre, T.; Bielawski, J.; Sundqvist, B.U.R. Int. J. Mass, Spectrom. Ion Proc. 1994, vol. 130, pp. 107-115.
S. J. Kim, K.H. Kang, J.G. Lee, I.S. Kang, and B.J. Yoon, Control of Particle-Deposition Pattern in a Sessile Droplet by using the Radial Electoosmotic Flow, poster and technical note presented at the Ninth International Conference on Miniaturized Systems for Chemistry and Life Sciences, on Oct. 10, 2005, Boston, MA (USA).
Deegan, R.D.; Bakajin, O.; Dupont, T.F.; Huber, G.; Nagel, S.R.; Witten, T.A. Nature 1997, 389, 827-829.
Hu, H.; Larson, R.G. J. Phys. Chem. B 2002, 106, 1334-1344.
Lee, J.G.; cho, H.J.; Huh, N.; Ko, C.; Lee, W.C.; Jang, Y.H.; Lee, B.S.; Kang, I.S.; Choi, J.W.; Biosensors and Bioelectronics 2006, vol. 21, pp. 2240-2247.
Lee, B.S.; cho, H.J.; Lee, J.G.; Huh, N.; Choi, J.W.; Kang, I.S. Journal of Colloid and Interface Science, 2006 in press.
Perera, I.K.; Perkins J.; Kantarzoglou, S. Rapid Commun. Mass Spectrom. 1995, vol. 9, pp. 180-187.

* cited by examiner

*Primary Examiner* — Harry D Wilkins, III
*Assistant Examiner* — Zulmariam Mendez
(74) *Attorney, Agent, or Firm* — Cantor Colburn LLP

(57) ABSTRACT

Provided is a device for controlling a particle distribution in a droplet including particles. The device includes: a first electrode for developing an electric field in the vicinity of the droplet; and a second electrode for developing the electric field that is fixed to a substrate, is insulated from the first electrode, and located at about the center of the droplet. A micro electrode system including a circular electrode placed along a droplet rim and a point electrode at about the center of the bottom is used to cause radial electroosmotic flow, thereby obtaining a uniform solute distribution after complete evaporation of the droplet. The direction and strength of the radial electroosmotic flow can be varied and the radial electroosmotic flow is periodically applied. Particles used to obtain uniformity are selected from the group consisting of a polymer, an organic substance, an inorganic substance, a metal, and a biomolecule. The particles can be neutral, negatively charged or positively charged.

3 Claims, 8 Drawing Sheets

(a)

(b)

(c)

(d)

DEVICE FOR CONTROLLING PARTICLE DISTRIBUTION IN AN EVAPORATING DROPLET USING RADIAL ELECTROOSMOTIC FLOW

CROSS-REFERENCE TO RELATED PATENT APPLICATION

This application claims the benefit of Korean Patent Application No. 10-2006-0008237, filed on Jan. 26, 2006, and all the benefits accruing therefrom under 35 U.S.C. §119, and the contents of which are incorporated herein by reference in their entirety.

BACKGROUND OF THE INVENTION

1. Field of the Invention

The present invention relates to a device for controlling particle distribution in an evaporating droplet using radial electroosmotic flow, and more particularly, to a device for controlling particle distribution in a droplet, including: a first electrode developing an electric field in the vicinity of the droplet; and a second electrode that develops an electric field, is fixed to a substrate, is insulated from the first electrode, and is located at about the center of the droplet.

2. Description of the Related Art

The dynamics of an evaporating droplet on a solid substrate has been studied for heat transfer applications, and the effects thereof are commonly observed in everyday life, for example, in the ring-like stain that remains after a coffee droplet evaporates. Recently, this simple phenomenon has been determined to be an essential mechanism in biological and analytical chemistry applications, especially in the case of applications in which there is exposure to the atmosphere. The importance of the evaporation process for the precise detection in a protein chip and a genomic DNA microarray or the successful analysis of DNA and protein using MALDI-TOFMS has been demonstrated. However, unexpected ring-patterned stain formation after complete evaporation of a droplet has become a key obstacle to efficient analysis. Such localization of a solute may result in the need for time to search for a sample spot that yields an abundant signal. This search is labor-intensive and time-consuming, and hinders automation of the analysis. Thus, it is desirable to devise a method for homogenizing the solute distribution inside a droplet after complete evaporation.

The physiochemical mechanism of a drop stain phenomenon has yet to be completely understood, but contact line pinning due to a hydrophilic surface and the non-uniform evaporation from the edge of the droplet might contribute to the outward migration of a solute. As the droplet remains pinned on the substrate and the liquid is removed from the edge of the droplet first, the outward flow from the interior must replenish the mass loss. The explanation for evaporation from the edge of a droplet that is considered most reasonable is that the probability of an evaporating molecule escaping at the edge of the droplet is higher than the probability of an evaporating molecule escaping from the center of the droplet due to the geometrical curvature of the droplet.

One way to improve spatial stain homogeneity is to develop a system which uses a substrate other than a bare metal or chemical surface treatment. The use of poly-tetrafluoroethylene and polymer/Nafion substrates was reported to produce a relatively homogeneous solute distribution (Kim, Y.; Hurst, G. B.; Doktycz, M. J.; Buchanan, M. V. *Anal. Chem.* 2001, 73, 2617-2624). Another possible way to produce a relatively homogeneous solute distribution is to control outward radial flow inside the droplet. Stirring and spin-coating sample preparation methods have been reported to achieve the control (Westman, A.; Demirev, P.; Huth-Fehre, T.; Bielawski, J.; Sundqvist, B. U. R. *Int. J. Mass. Spectrom. Ion Proc.* 1994, 130, 107-115 and Perera, I. K.; Perkins, J.; Kantartzoglou, S. *Rapid Commun. Mass Spectrom.* 1995, 9, 180-187). However, the surface treatment and the sample preparation techniques have shortcomings which give rise to an uncontrollable deposition pattern during experimental processes. Therefore, there is a need for a coating method that maintains a uniform surface regardless of whether the surface is hydrophobic or hydrophilic, that removes non-uniformity commonly found during the spotting and coating, etc., and that is a proper coating method for a metal-coated surface.

BRIEF SUMMARY OF THE INVENTION

In an embodiment of the present invention, there is provided a device for controlling particle distribution in a droplet, in which the device includes a first electrode for developing an electric field in the vicinity of the droplet; and a second electrode for developing the electric field in the vicinity of the droplet, where the second electrode is fixed to a substrate, is insulated from the first electrode, and the second electrode is located at about the center of the droplet.

In another embodiment, a method for using the device for controlling the particle distribution in a droplet comprising particles, comprises disposing a droplet comprising particles on the device for controlling the particle size distribution, where the device comprises a first and a second electrode as described herein, and the second electrode is located at about the center of the droplet; and applying a voltage to the first and second electrodes to generate an electrical field.

In another embodiment, a method of controlling particle distribution in a droplet comprising particles comprises applying an electric field to a device for controlling the particle distribution in the droplet comprising particles. In the method, the inward or outward radial electroosmotic flow of the particles inside the droplet is induced according to the characteristics of the particles.

BRIEF DESCRIPTION OF THE DRAWINGS

The above and other features and advantages of the present invention will become more apparent by describing in detail exemplary embodiments thereof with reference to the attached drawings in which:

FIG. 1A is a cross-sectional view illustrating a simplified fabrication process of an electrode;

FIG. 1B is a plan view of a mask for center electrode patterning;

FIG. 1C is a plan view of a mask for silicon deposition to prevent a short circuit;

FIG. 1D is a plan view of a mask for circular electrode patterning;

FIG. 2A is a picture of electrode systems with radii of 0.5 mm, 1 mm, 1.5 mm, and 2 mm according to an embodiment in a single silicon wafer;

FIG. 2B is a picture of an electrode system according to an embodiment connected to an external power-supplying device;

FIG. 3 is a schematic diagram of an evaporating droplet in a cylindrical coordinate system in which (r, z) and R, $h_0$ and Θ are respectively the droplet radius, center height, and contact angle; J(r, t) is the non-uniform evaporation rate on the droplet surface as a function of the radial position and time; and h(r, t) is the local droplet;

Figure 1:
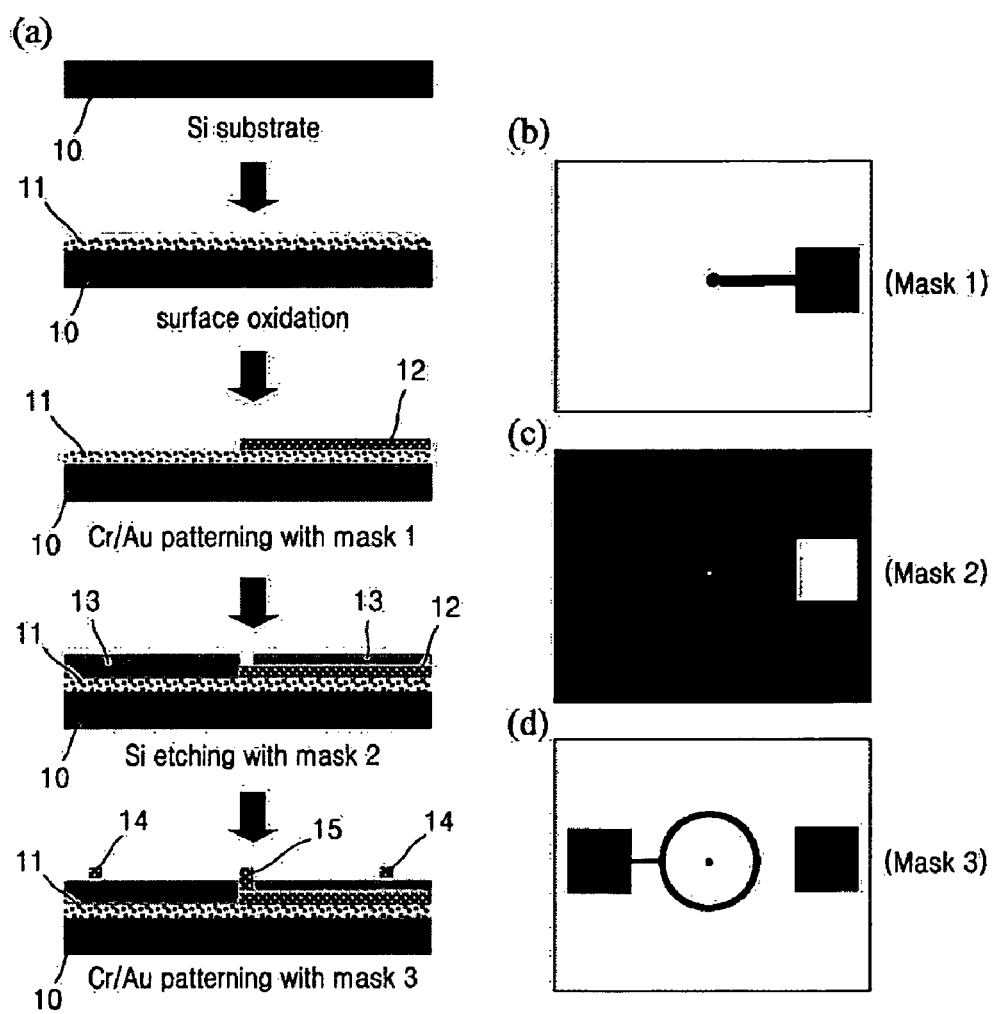

FIG. 11B illustrates a droplet stain after evaporation on an electrode with a radius of 1 mm, of a droplet including negatively charged carboxylic acid latex particles when inward radial electroosmotic flow is induced (DC 1.0V+AC 0.8V); and FIG. 11C illustrates a droplet stain after evaporation on an electrode with a radius of 1 mm, of a droplet including negatively charged carboxylic acid latex particles when inward radial electroosmotic flow is induced (DC 1.4V+AC 0.8V).

DETAILED DESCRIPTION OF THE INVENTION

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

It will be understood that when an element is referred to as being "on" another element, it can be directly on the other element or intervening elements may be present therebetween. In contrast, when an element is referred to as being "deposited on" another element, the elements are understood to be in at least partial contact with each other, unless otherwise specified.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

A device for controlling a particle distribution in a droplet according to an embodiment of the present invention includes a first electrode for generating an electric field in the vicinity of the droplet containing particles, and a second electrode for developing the electric field, which is fixed on a substrate, is insulated from the first electrode, and is located at about the center of the droplet.

Radial electroosmotic flow as an effective means for controlling liquid flow inside a droplet has been demonstrated Kim et. al. (S. J. Kim, K. H. Kang, J. G. Lee, I. S. Kang, and B. J. Yoon, "Control of Particle-Deposition Pattern in a Sessile Droplet by using the Radial Electroosmotic Flow" poster and technical note presented at the *Ninth International Conference on Miniaturized Systems for Chemistry and Life Sciences*, on Oct. 10, 2005, Boston, Mass. (USA)), the disclosure of which is incorporated herein in its entirety. In Kim et. al., a circular electrode system in which a point electrode is disposed in the center of a circle formed by a circular electrode is provided. An electric field generated between the point electrode and the circular electrode, which is placed along the droplet rim, causes radial electroosmotic flow in the vicinity of the bottom of the droplet. By changing the polarity and the strength of an applied voltage, the radial direction (inward or outward) and magnitude of the radial electroosmotic flow can be controlled, and thus the solute distribution inside the droplet can be modified as required. Periodic applications of an electric field can uniformly distribute solutes and shorten the drying time of the droplet, and thus the analysis of particles can easily be performed. With this device, the homogeneous deposition on a substrate is possible and the solutes are collected into the center of the droplet according to the applied voltage.

Figure 2:
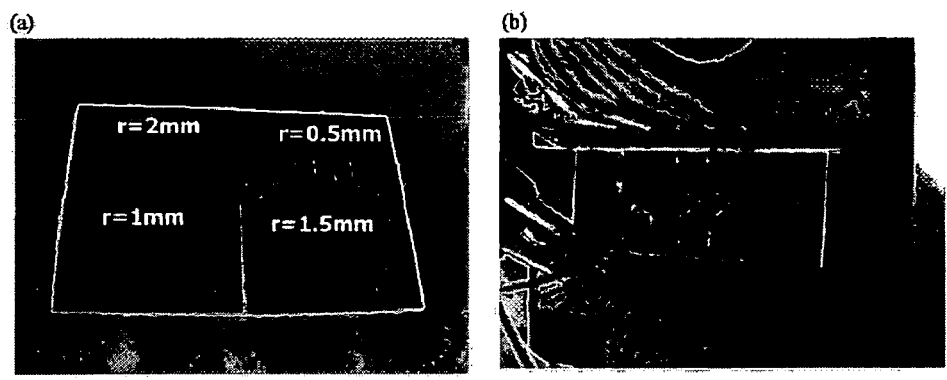

FIG. 2 is a photograph of a device for controlling microdroplets according to an embodiment. The device for controlling particle distribution in a droplet can control droplets generally, and more specifically can control microdroplets. As shown in FIG. 2, the device includes a circular electrode placed along a droplet rim (a first electrode for generating an electric field) and a point electrode at about the center of the droplet (a second electrode for generating the electric field). The first electrode for generating an electric field may be circular, oval, triangular or rectangular, but the shape is not limited thereto. An electric field generated between the point electrode, also referred to herein as the center electrode, and the circular electrode causes radial electroosmotic flow in the vicinity of the bottom of droplet. In a method, by changing the polarity and the strength of an applied voltage, the radial direction (inward and outward) and magnitude of the radial electroosmotic flow can be controlled, and the particle or solute distribution inside the droplet can be modified as required. Also in this way, a method for using the device for controlling the particle distribution in a droplet comprising particles includes placing a droplet at about the center of the point electrode, and applying a voltage across the center and circular electrodes to provide an electric field.

The point electrode is fixed on a substrate and insulated from the circular electrode by an insulating layer. The point electrode and the circular electrode are connected to an earth (i.e., electrical grounding) plate by a lead line and voltage is supplied to both electrodes by connecting the earth plate to a voltage supply. The electric field developed between the point electrode and the circular electrode placed along the droplet rim causes radial electroosmotic flow in the vicinity of the bottom of the droplet.

In an embodiment, the voltage supply can simultaneously apply an alternating voltage and a direct voltage to the electrodes to provide the electric field. The voltage supply may independently apply an alternating voltage or a direct voltage to induce a uniform droplet distribution. However, the simultaneous application of the alternating voltage and the direct voltage can induce more uniform droplet distribution. Use of the direct voltage by itself may damage a biomolecule in the droplet or a microelectrode pattern in contact with the droplet and/or electrodes. Thus, the direct voltage is used together with the alternating voltage. An alternating electric field having a high frequency of greater than 1 kHz stabilizes the motion of particles inside the droplet, minimizes the movement toward the rim of droplet, and thus results in a uniform stain. An alternating electric field having a low frequency around 100 Hz smoothes the flow inside the droplet, increasing the chances of contact of the solvent to be evaporated from the droplet with the external environment, and thus the alternating electric field can decrease the time required for evaporation.

According to an embodiment, inward radial electroosmotic flow or outward radial electroosmotic flow may be provided according to the characteristics of the particles in the droplet. The direction of the radial electroosmotic flow of the particles inside the droplet can be inward or outward according to the direction of the voltage applied by the voltage supply, and the surface charge of the particle. For example, when the surface of the particle is negatively charged, the point electrode has a lower electrical potential than the circular electrode, the direction of the particle inside droplet is outward. That is, the particles can be moved as required according to the electric potentials of the point electrode and the circular electrode and the characteristics of the particles in the droplet.

The particles may have a diameter of 10 nm to 5 μm. When the size of the particle is outside of this range, the desired movement of particles by the radial electroosmotic flow cannot easily be obtained.

The particles may comprise, but are not limited to, a polymer, an organic substance, an inorganic substance, a metal, or a biomolecule.

The particles may be neutral, positively charged, or negatively charged. The direction of particle flow inside the droplet can be controlled inward or outward according to the characteristics of the particle.

The electric potential difference between the first and second electrodes for generating the electric field may be 1 mV to 5 V. When the electrical potential difference is less than 1 mV, the applied voltage is insufficient to induce the particles to flow. When the electrical potential difference is greater than 5 V, the particles become less easily differentiated by size and/or charge, and hence a uniform distribution of the particles cannot easily be obtained.

An alternating voltage with a frequency in the range of 1 Hz to 10 kHz can be applied to the first and second electrodes generating an electric field. When the frequency is less than 1 Hz, the applied voltage will hardly cause the particles to flow. When the frequency is greater than 10 kHz, a uniform distribution of the particles cannot easily be obtained.

The waveform of the alternating voltage applied to the first and second electrodes developing an electric field may be a sine waveform, a square waveform, a pulse waveform, or a triangular waveform, but is not limited thereto.

The first and second electrodes developing an electric field may be composed of a conductive metal, a conductive polymer composition, or ITO glass. Examples of the conductive metal include Au, Cr, Pt, Pd, and Ni, and examples of the polymers for use in the conductive polymer composition include acrylonitrile, butadiene, styrene, polyvinyl chloride, polycarbonate, polyphenylene resin, polyethylene, polypropylene, nylon, thermoplastic polyester, polystyrene, and other conductive polymers such as polythiophene, polyaniline, and the like.

The substrate may be composed of silicon, glass or a polymer, but is not limited thereto.

The present invention will be described in further detail with reference to the following examples. These examples are for illustrative purposes only and are not intended to limit the scope of the present invention.

EXAMPLE 1

Preparation of Electrode

A four-inch silicon wafer was used to fabricate a circular electrode system. Prior to micro-fabrication of the silicon wafer, the wafer 10 was cleaned to remove contaminants. FIG. 1a schematically illustrates a simplified fabrication process, together with the masks used. First, the surface of the silicon wafer 10 was oxidized to form an oxide layer 11 on a surface of the silicon wafer 10 to prevent a short circuit. A thin patterned positive-tone resist film was then used as a sputter mask (with the transferable pattern shown in black in FIG. 1b) to allow sputtering of the correspondingly patterned center electrode 12 using a combination of Cr and Au. The thickness of the patterned Cr/Au substrate layer electrode 12 was 1 μm. The substrate layer electrode 12, so prepared, is buried beneath the circular electrode 14. A silicon oxide insulation layer 13 was then deposited on the substrate electrode 12 and oxide layer 11 to provide a dielectric insulation between the substrate electrode 12 and the circular electrode 14 and thereby prevent a short circuit. The insulation layer 13 was patterned by etching according to a negative-tone patterned film etch mask such as that shown in FIG. 1c (in which the light areas correspond to the etched patterns). Finally, the circularly patterned Cr/Au circular electrode 14 and its bond pad (not shown), and the center electrode 15 physically and electrically connected to the substrate electrode 12 were deposited to a height of 1 μm using a positive-tone sputter mask as shown in FIG. 1d (in which the dark areas correspond to the transferable patterns). The circular electrodes 14 were fabricated in a single silicon wafer with radii of 1 mm, 2 mm, and 5 mm. The completed electrode systems are shown in FIG. 2.

EXAMPLE 2

System Setup Including Sample Liquid

A colloidal suspension of surfactant-free, 50 nm polystyrene micro-spheres in 0.01 M NaCl solution was used as a deposition pattern tracer (A Johnson Matthey Company). A NaCl solution as an electrolyte was used to form a droplet to induce electroosmotic flow and the electrical double layer thickness was less than 10 nm at this concentration. Although the polystyrene particles had a slightly negative charge, they were regarded as neutral. The electrophoretic motion of the polystyrene particles was sufficiently small to assume that the electrophoretic effect could be neglected. The experiment was carried out using deionized water as the solvent, i.e., without an electrolyte solution, to test the electrophoretic motion of polystyrene particles. In the deionized water, the resulting deposition pattern was the same as that formed during natural evaporation in both inward-radial and outward-radial electric field conditions. The flow velocity caused by the natural convection was about 40 μm/sec. Since the external applied voltage had a maximum value of 1.5 V in this system, the electrophoretic mobility of the slightly negatively charged polystyrene particles was less than 1 μm/sec. Therefore, the polystyrene particles were regarded as neutrally charged particles. Although gravitational force and a temperature gradient do not play an important role in the formation of ring stain, the substrate was kept horizontal during the experiments and the temperature was maintained at room temperature. The diffusion of a solute could be neglected since the Peclet number is far greater than 100 (Pe=ULID=40μm/sec×1 mm/$10^{-12}$m²/sec=4×$10^4$). The dielectrophoretic effect was also neglected since DC electric fields were used. The performance of the circular electrode was captured using a digital camera (Optio4, PENTAX) at 30 second intervals. A micropipette was used to drop droplets with a volume of 1 μl into the circular electrodes with a radius of 1 mm, and thus an initial contact angle of 60 degrees was assumed, under the assumption that the shape of the droplet was a spherical cap. Under these conditions, the droplets completely evaporated within 20 minutes. The experiments were performed voltages of various strength and polarity to investigate the effects of radial electroosmotic flow.

EXAMPLE 3

Theoretical Modeling

Scale Statement

The droplet shape depends on the bond number, Bo=ρgRh₀/σ, which is the ratio of the surface tension to the gravitational force on the droplet, and the capillary number Ca=μu/σ, which is the ratio of the viscosity to the capillary force. Here, ρ represents the fluid density, μ represents the fluid viscosity, σ represents the interfacial tension at an air-fluid interface, g represents gravitational acceleration, R represents the contact-line radius, h₀ represents the initial height of the droplet, and u represents the average radial velocity induced by droplet evaporation. The contact-line radius of the droplet system was about 1.0 mm and the flow velocity inside droplet was less than 40 μm/sec. Consequently, the Bond number was approximately 0.07 and the capillary number was around $10^{-8}$, and thus that the droplet shape could be regarded as a spherical cap. In addition, the flow field inside a droplet is governed by Stokes equation, $0 = -\nabla p + \mu \nabla^2 u$, and the continuity equation, $\nabla \cdot u = 0$. The flow boundary conditions are a no-slip condition during natural evaporation cases and the Smoluchowski slip condition when radial electroosmotic flow is induced.

Analytical Solution of 2D Flow Field in an Evaporation Droplet

Figure 3:
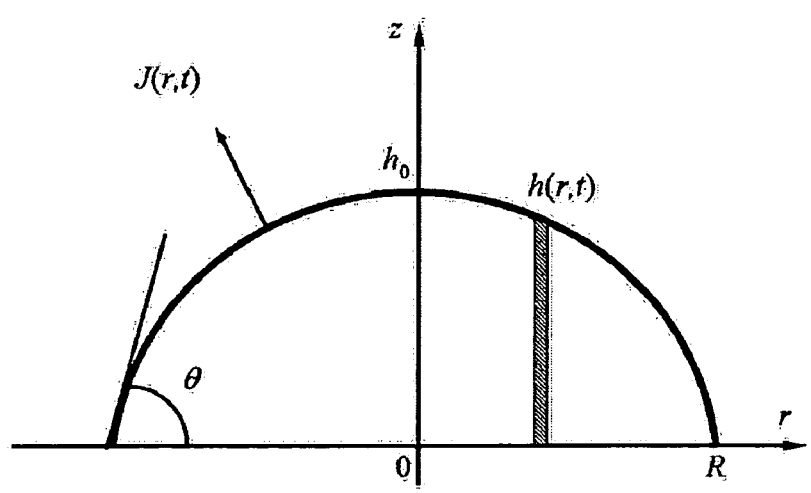

A small spherical-cap-shaped droplet of water on a solid substrate was considered (See FIG. 3). A (r, ρ, z) cylindrical coordinate system, which has its origin at the center of the base circle of the droplet, was introduced. Due to axial symmetry, there is no change of parameters in the ρ-direction, i.e. $\delta/\delta\rho = 0$. Accordingly, the continuity and Stokes equations can be written in cylindrical coordinates as follows:

$$\frac{1}{r}\frac{\partial}{\partial r}(ru_r) + \frac{\partial u_z}{\partial z} = 0, \tag{1}$$

$$\mu\left(\frac{\partial}{\partial r}\left(\frac{1}{r}\frac{\partial}{\partial r}(ru_r)\right) + \frac{\partial^2 u_r}{\partial z^2}\right) = \frac{\partial p}{\partial r}, \tag{2}$$

$$\mu\left(\frac{1}{r}\frac{\partial}{\partial r}\left(r\frac{\partial u_z}{\partial r}\right) + \frac{\partial^2 u_z}{\partial z^2}\right) = \frac{\partial p}{\partial z} \tag{3}$$

where $u_r$ and $u_z$ represent the velocity component in the r and z directions, respectively.

The local height h(r, t) of the spherical droplet is determined from the contact angle Θ and the contact radius R as follows:

$$h(r,t) = \sqrt{R^2/\sin^2\theta - r^2} - R/\tan\theta, \quad r \leq R. \tag{4}$$

In previous studies done by Deegan, et al. (Deegan, R. D.; Bakajin, O.; Dupont, T. F.; Huber, G.; Nagel, S. R.; Witten, T. A. *Nature* 1997, 389, 827-829.) and Larson, et al. (Hu, H.; Larson, R. G. *J. Phys. Chem. B* 2002, 106, 1334-1344.), 2-dimensional velocity fields inside the droplet have been found to be:

$$\tilde{u}_r = \frac{3}{8}\frac{1}{1-\tilde{t}}\frac{1}{\tilde{r}}\left[(1-\tilde{r}^2) - (1-\tilde{r}^2)^{-\lambda(\theta)}\right]\left(\frac{\tilde{z}^2}{\tilde{h}^2} - 2\frac{\tilde{z}}{\tilde{h}}\right), \tag{5}$$

$$\tilde{u}_z = \frac{1}{4}\frac{1}{1-\tilde{t}}\left[1 + \lambda(\theta)(1-\tilde{r}^2)^{-\lambda(\theta)-1}\right]\left(\frac{\tilde{z}^3}{3\tilde{h}^2} - \frac{\tilde{z}^2}{\tilde{h}}\right) + \tag{6}$$

$$\frac{3}{2}\frac{1}{1-\tilde{t}}\left[(1-\tilde{r}^2) - (1-\tilde{r}^2)^{-\lambda(\theta)}\right]\left(\frac{\tilde{z}^2}{2\tilde{h}^2} - \frac{\tilde{z}^3}{\tilde{h}^3}\right)\tilde{h}(0,t)$$

where the dimensionless variables are defined as follow:

$$\tilde{r} = \frac{r}{R}, \tilde{z} = \frac{z}{h_0}, \tilde{h} = \frac{h}{h_0}, \tilde{t} = \frac{t}{t_f}, \tilde{u}_r = \frac{u_r t_f}{R}, \tilde{u}_z = \frac{u_z t_f}{h_0}.$$

and λ(Θ) is an experimental parameter given by 0.5−Θ/π reflecting the non-uniformity of evaporation, t is the time spent drying, $t_f$ is the total drying time, and $\tilde{t}$ is the fraction of drying time such that drying is initiated at $\tilde{t}=0.0$, is half complete at $\tilde{t}=0.5$, and is complete at $\tilde{t}=1.0$.

Figure 4:
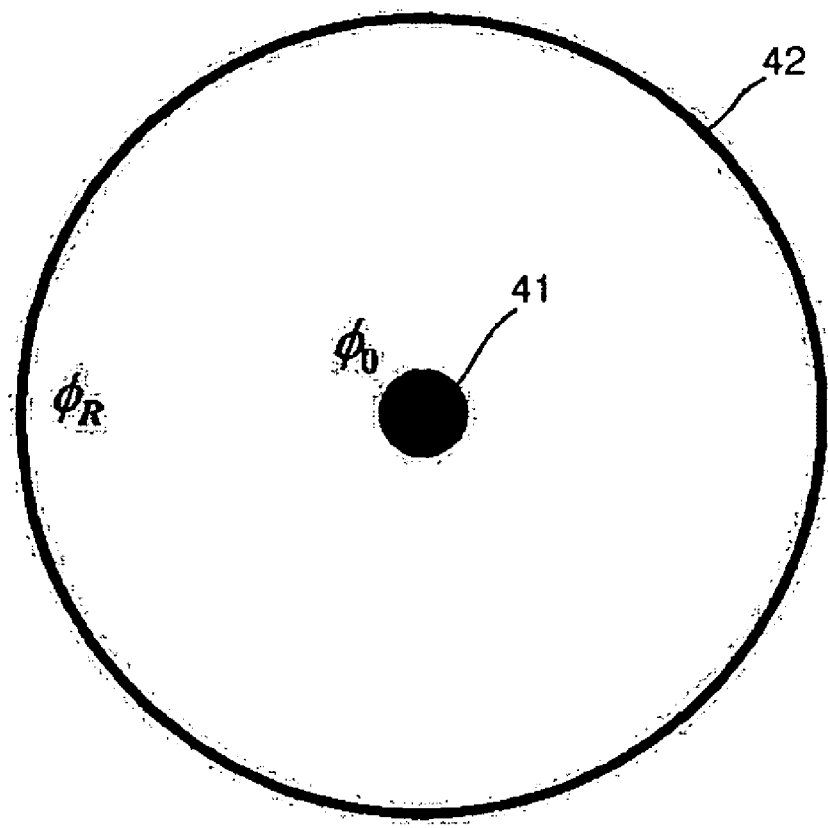
FIG. 4 is a schematic configuration of center and circular electrodes near the bottom surface of an evaporating droplet $\phi_0$ and $\phi_R$ are respectively the electrical potential at the center electrode 41 and the rim electrode 42.

Natural flow inside a droplet due to evaporation satisfies the no-slip flow condition at the liquid/substrate interface. However, a slip flow condition is applicable when electroosmotic flow is induced inside the droplet. The electroosmotic slip condition is valid in the case of a thin electrical double layer. The thickness of electrical double layer is determined by various factors, the most important factor being the concentration of a bulk electrolyte (higher electrolyte concentration resulting in thinner electrical double layer). A sufficiently high electrolyte concentration to use the slip velocity approximation was used. To apply the slip-velocity boundary condition due to electroosmosis, the electric field distribution in the vicinity of the substrate surface should be determined. FIG. 4 shows the configuration of the center electrode 41 and circular electrode 42 near the bottom surface of the droplet. $\phi_0$ and $\phi_R$ are the electrical potentials at the center and circular electrodes, respectively. If the electrolyte concentration is uniform inside the droplet, the electric field satisfies $\nabla \cdot E = 0$, which is merely the current conservation requirement, and the electric potential satisfies the Laplace equation in polar coordinates, and is thus a logarithmic function. Because the electric field is equal to the negative gradient of the electrical potential, $E = -\nabla \phi$, the non-uniform electric field distribution is proportion to $1/r$ under the lubrication assumption that the variations in the z-direction can be neglected.

Under this assumption, the radial velocity, $\tilde{u}_r$, was first considered. A constant times $1/r$ term was inserted into equation (5) to obtain $\tilde{u}_r$ with the electroosmotic slip velocity on the substrate surface as follow:

$$\tilde{u}_r = \frac{3}{8}\frac{1}{1-\tilde{t}}\frac{1}{\tilde{r}}[(1-\tilde{r}^2)-(1-\tilde{r}^2)^{-\lambda(\theta)}]\left(\frac{\tilde{z}^2}{\tilde{h}^2}-2\frac{\tilde{z}}{\tilde{h}}\right)+\frac{\alpha}{\tilde{r}} \quad (7)$$

where $\alpha$ is the strength parameter of the electroosmotic velocity determined by the following equation:

$$\alpha = \frac{\varepsilon\zeta|E|}{\mu}\Big/u_e^{avg} \quad (8)$$

where $u_e^{avg}$ is the average radial electroosmotic velocity, which can be obtained by integrating $1/r$ from the center to the rim of the droplet. On the substrate, the radial velocity is exactly proportional to the electric field, and the strength of the electric field depends on the surface zeta potential and the external electric field strength. The axial velocity, $\tilde{u}_z$, is obtained using the continuity equation (1), and has the formula shown in equation (6). Also, the $1/r$ term in equation (7) satisfies both the continuity equation (1) and Stokes equation (both the general and specific equations (2) and (3)) because the differentiation of $r \times \alpha/r$ with respect to r vanishes to zero. Finally, the full 2-dimensional radial and axial electroosmotic velocity field given by equations (7) and (6) can be used respectively. However, when the particle is negatively or positively charged, the flow field should be re-analyzed considering the electrophorous effect including the motion of the particles.

EXAMPLE 4

Natural Evaporation

Figure 5:
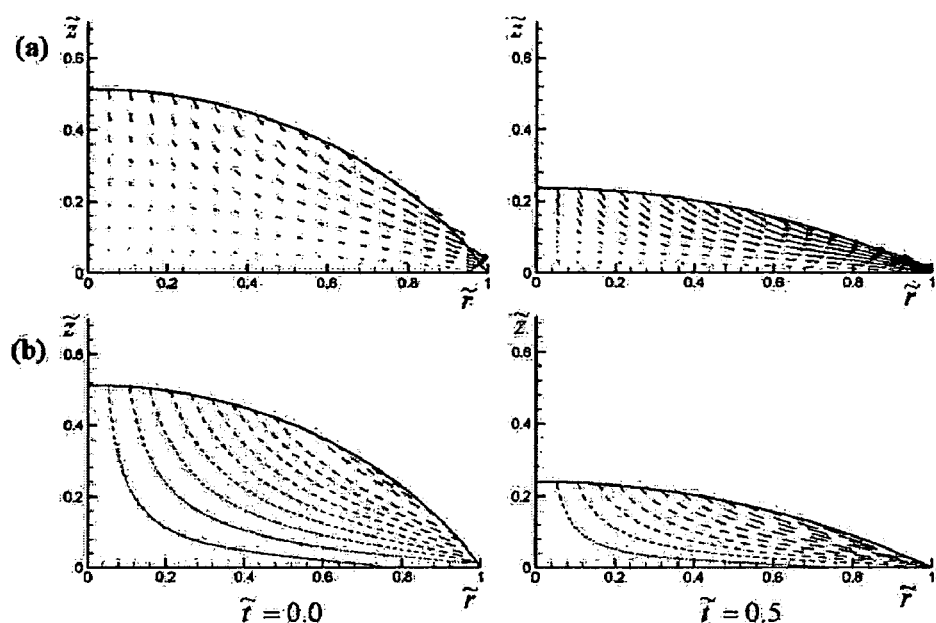
FIG. 5A illustrates a cross-sectional flow field inside an evaporating droplet under natural drying conditions of $\tilde{t}=0.0$ and $\tilde{t}=0.5$.
FIG. 5B illustrates a cross-sectional stream line inside an evaporating droplet under natural drying conditions of $\tilde{t}=0.0$ and $\tilde{t}=0.5$.
Figure 6:
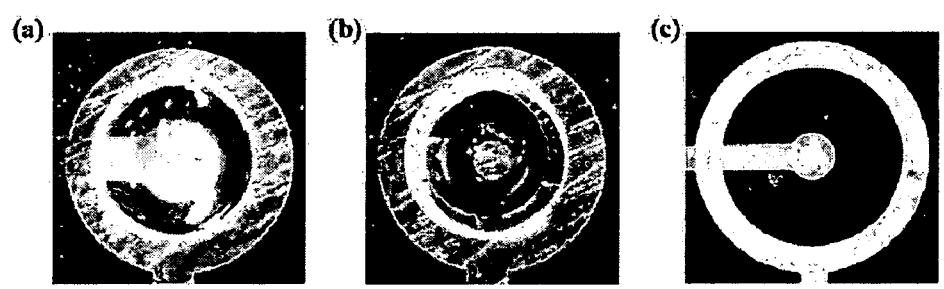
FIG. 6A is a photograph of a drop stain obtained after droplet evaporation of a polystyrene droplet on an electrode having a 1 mm radius without electroosmosis when $\tilde{t}=0.0$.
FIG. 6B is a photograph of a drop stain obtained after droplet evaporation of a polystyrene droplet on an electrode with a 1 mm radius without electroosmosis when $\tilde{t}=1.0$.
FIG. 6C is a photograph of a drop stain obtained after droplet evaporation of a polystyrene droplet on an electrode with a 2 mm radius without electroosmosis when $\tilde{t}=1.0$.

The cross-sectional flow field and stream line inside a droplet under natural drying conditions were theoretically computed by equation (7) and (6) and are shown in FIG. 5. FIG. 5 shows that the flow near the center (z-axis at r=0) has a dominant vertical component (small arrows in the plot), and the magnitude of flow near the rim (r axis at z=0) is strongest due to the maximum evaporation rate at the edge. Also the magnitude of outward radial flow accelerates according to evaporation time. Consequently, a polystyrene particle which starts at the liquid/gas interface goes moves down and then toward the rim of the droplet. FIG. 6 shows the experimental results of evaporating drop stain without electroosmotic flow, i.e. $\alpha$ is zero in equation (7). The initial droplet is shown in FIG. 6a and a ring-like stain is clearly observed after complete evaporation as shown in FIG. 6b. A coffee stain on an electrode with a radius of 2 mm is shown in FIG. 6c. While many unknown substances were contained in the coffee particles, the ring-shape deposition pattern around rim could also be observed.

EXAMPLE 5

Effect of Radial Electroosmotic Flow

Figure 7:
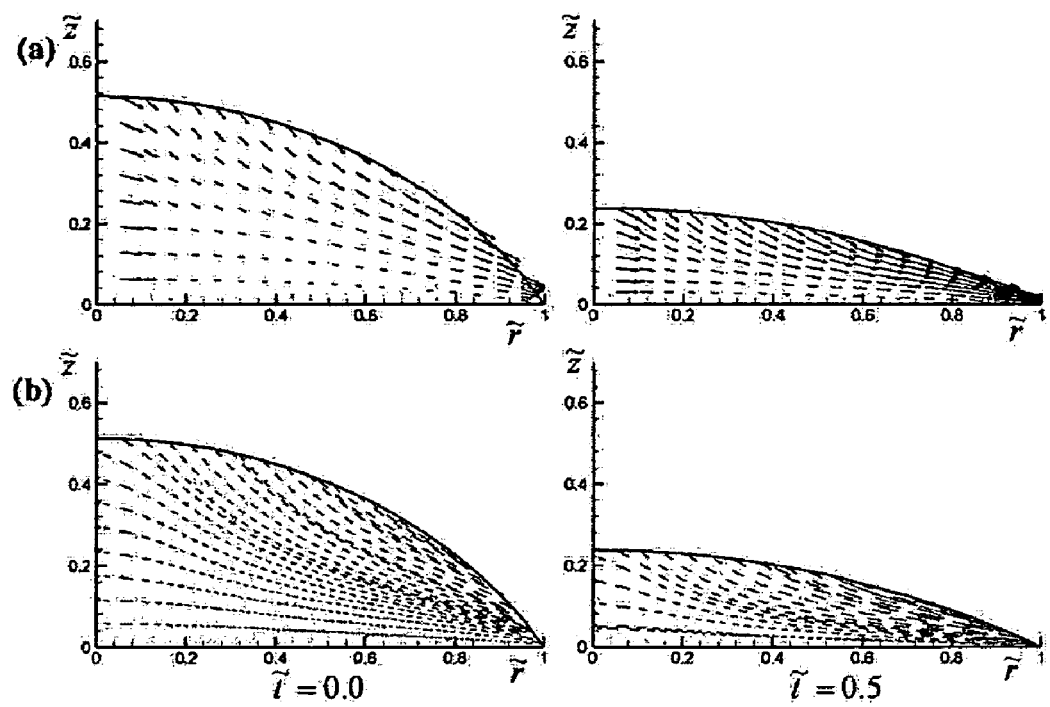
FIG. 7A is a cross-sectional flow field inside a droplet at $\tilde{t}=0.0$ and $\tilde{t}=0.5$ when outward radial electroosmotic flow is induced ($\alpha=0.025$)
FIG. 7B is a cross-sectional stream lime inside a droplet at $\tilde{t}=0.0$ and $\tilde{t}=0.5$ when outward radial electroosmotic flow is induced ($\alpha=0.025$)
Figure 8:
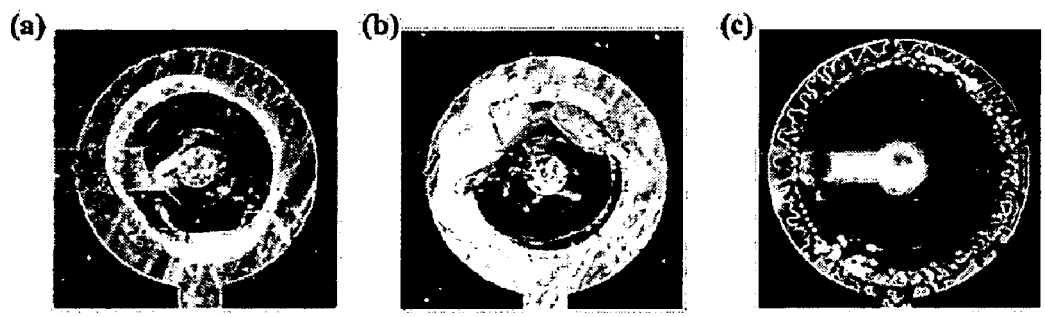
FIG. 8A is a photograph of a drop stain after complete evaporation when outward radial electroosmotic flow is induced ($\alpha=0.025$)
FIG. 8B is a photograph of a drop stain after complete evaporation when outward radial electroosmotic flow is induced ($\alpha=0.050$)
FIG. 8C is a photograph of a coffee stain on an electrode with a radius of 2 mm after complete evaporation when outward radial electroosmotic flow is induced ($\alpha=0.050$)

The flow field and stream lines inside a droplet are shown in FIG. 7 when the outward radial electroosmotic flow helped the outward natural flow. The strength parameter of electroosmotic flow, $\alpha$, was 0.025 ($|E|=600$ V/m). Since the electroosmotic flow is stronger at the center (z axis at r=0) than at the edge (i.e., rim; r axis at z=0) of the droplet, the total flow field (sum of natural flow and electroosmotic flow) at the center has a dominant horizontal component toward the edge of the droplet. Also, the electroosmotic flow helps transport the solute to the edge. Consequently, thicker depositions than those obtained with the natural evaporation were experimentally observed when various outward electroosmotic flows were used, as shown in FIG. 8. The value of $\alpha$ was 0.025 ($|E|=600$ V/m) in FIG. 8a and 0.050 in FIGS. 8b and 8c ($|E|=1200$ V/m). FIG. 8c illustrates the case of a coffee stain on an electrode with a radius of 2 mm. Denser depositions are observed under the stronger outward electroosmotic flow condition than under the natural evaporation condition.

Figure 9:
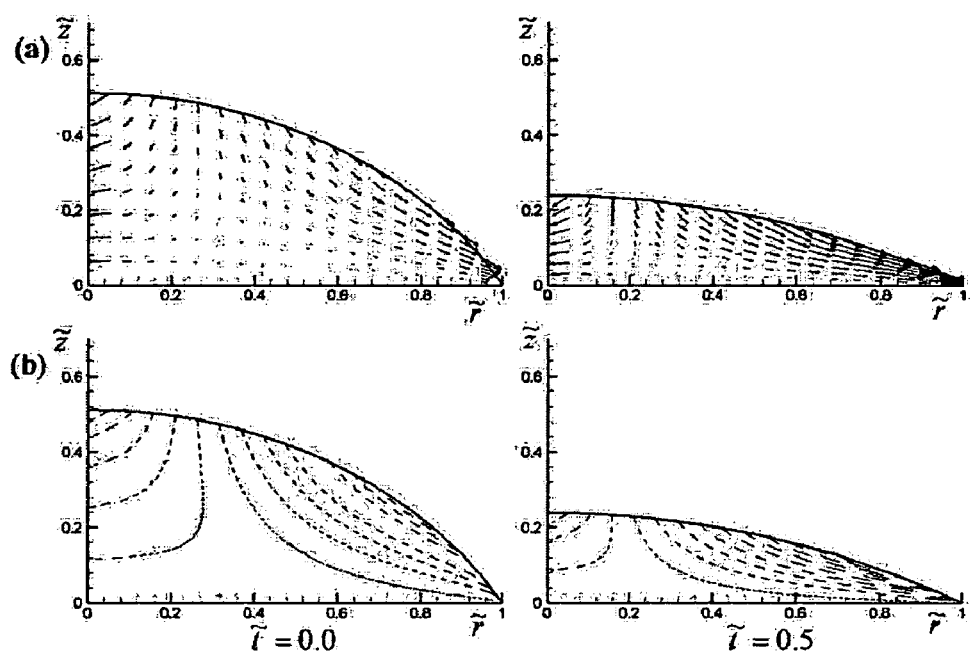
FIG. 9A is a cross-sectional flow field inside a droplet at $\tilde{t}=0.0$ and $\tilde{t}=0.5$ when there is inward radial electroosmotic flow ($\alpha=-0.025$)
FIG. 9B is a cross-sectional stream line inside a droplet at $\tilde{t}=0.0$ and $\tilde{t}=0.5$ when there is inward radial electroosmotic flow ($\alpha=-0.025$)
Figure 10:
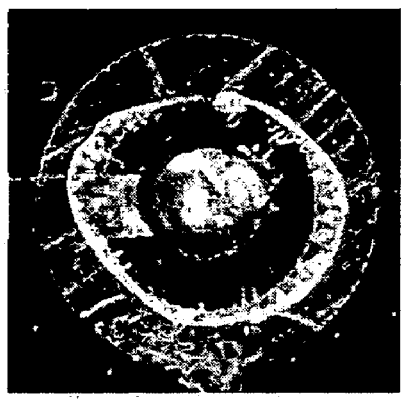
FIG. 10A is a photograph of a drop stain after complete evaporation when inward radial electroosmotic flow is induced ($\alpha=-0.025$)
FIG. 10B is a photograph of a drop stain after complete evaporation when inward radial electroosmotic flow is induced ($\alpha=-0.050$)
FIG. 10C is a photograph of a coffee stain on an electrode with a radius of 2 mm after complete evaporation when inward radial electroosmotic flow is induced ($\alpha=-0.025$)
FIG. 10D is a photograph of a coffee stain on an electrode with a radius of 2 mm after complete evaporation when inward radial electroosmotic flow is induced ($\alpha=-0.050$)
Figure 10:
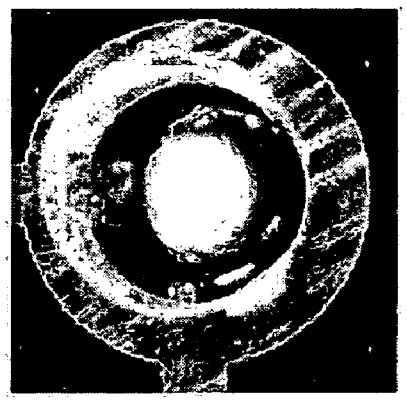
Figure 10:
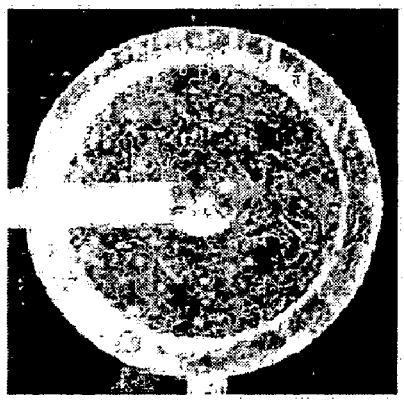
Figure 10:
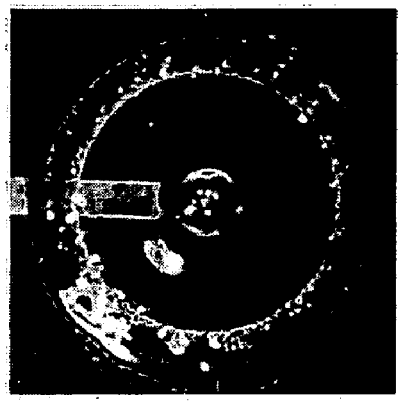

In contrast to outward flow, FIG. 9a shows the flow field and stream line when there is an inward radial electroosmotic flow with $\alpha=-0.025$ ($|E|=600$ V/m). The stream lines separate around $\tilde{r}=0.4$ due to the stronger inward electroosmotic flow near the center, as shown in FIG. 9b. As time passes, the separate get closer to the center of the droplet as shown in the second drawing of FIG. 9b, and this gives arise to the separated solute deposition pattern in experimental results. In this inward case, important features are observed according to the strength of electroosmotic flow. The ring shaped solute deposition around the edge obtained with the weak inward electroosmotic flow is fairly similar to that obtained in the case of natural drying. However, the solute collects in the center of droplet as the inward electric field increases. It can be easily noticed that a uniform solute deposition can be obtained when the electric field has a specific strength. FIG. 10 shows the experimental particle deposition patterns at various electroosmotic flow strengths. When $\alpha$ is $-0.025$ ($|E|=600$ V/m), homogeneous deposition patterns shown in FIGS. 10a and 10c were obtained. When $\alpha=-0.050$ and $|E|=1200$ V/m, the solute concentrated in the center instead of around the edge as shown in FIGS. 10b and 10d. FIGS. 10c and 10d illustrate particle deposition patterns of coffee on an electrode with a radius of 2 mm. FIGS. 10b and 10d show the separated deposition patterns which resulted from the strong inward electroosmosis. Since the radial flow is separated around $\tilde{r}=0.4$ which is as predicted by FIG. 9b, the solutes are deposited at not only the center, but also the rim of droplet.

EXAMPLE 6

Effect of Periodic Electric Field and Negatively Charged Particle

Figure 11:
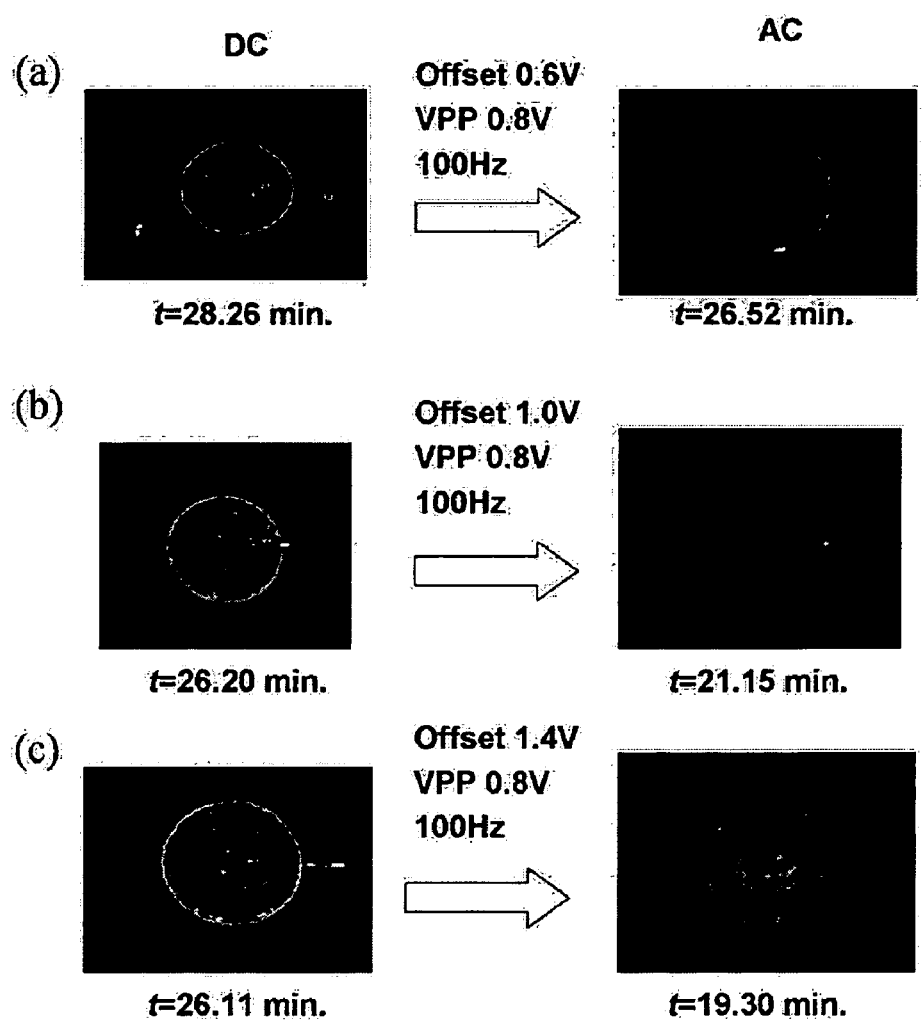
FIG. 11A illustrates a droplet stain after evaporation on an electrode with a radius of 1 mm, of a droplet including negatively charged carboxylic acid latex particles when inward radial electroosmotic flow is induced (DC 0.6V+AC 0.8V)

FIG. 11 illustrates drying tendencies of surfactant-free yellow carboxylic acid latex particles (0.31 μm, available from Molecular Probes-Invitrogen Inc.). Inward electroosmotic flow was caused by applying an alternating voltage having a peak to peak distance of 0.8 and direct voltages of 0.6 V, 0.8 V and 1.4 V to an electrode having a 1 mm radius. As illustrated in FIG. 11, the particles were distributed in the vicinity of the droplet in FIG. 11a, the particles were uniformly distributed in FIG. 11b, and the particles were simultaneously distributed in the center and the vicinity of the droplet in FIG. 11c. $\alpha$ was respectively 0.025, 0.033 and 0.058 in FIGS. 11a through 11c. The uniform distribution can be obtained when $\alpha$ is 0.033. When the particles were not charged, the uniform distribution was obtained when $\alpha$ was 0.025. However, when the particle were charged, for example, negatively charged, the charged particle flow depended on the electric field, and thus the proper value of $\alpha$ varied. The strength of the electric field which gave uniform particle distribution usually did not exceed 5 V/mm. In practical uses, a method of changing strengths of external electric field to control particle distributions according to the characteristics of the particles to be analyzed is more common than a method of surface treatment, or the like. An appropriate external voltage for application to an actual analysis device can be determined though experimentation. When an alternating electric field with a frequency of 100 Hz was applied, the amount of time to dry a droplet decreased by 2 to 7 minutes. Therefore, the time required to dry a droplet can be decreased using the device.

According to the present invention, a micro electrode system including a circular electrode placed along a droplet rim and a point electrode placed at the center of the droplet is used to cause radial electroosmotic flow, thereby obtaining a uniform solute distribution after complete evaporation of the droplet.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for using a device for controlling the particle distribution in a droplet comprising particles, comprising
    disposing a droplet comprising particles on an electrode of the device for controlling the particle size distribution, wherein the device comprises
    a first electrode for developing an electric field in the vicinity of the droplet; the first electrode being disposed on a substrate; and
    a second electrode for developing the electric field in the vicinity of the droplet, wherein the second electrode is fixed to the substrate, is insulated from the first electrode, and wherein the second electrode is located at about the center of the droplet; where the first electrode surrounds the second electrode; and
    applying a voltage to the first and second electrodes to generate an electrical field.

2. A method of controlling particle distribution in a droplet comprising particles, comprising
    applying an electric field to a device for controlling the particle distribution in the droplet comprising particles, the device comprising:
    a first electrode for developing the electric field in the vicinity of the droplet; the first electrode being disposed on a substrate; and
    a second electrode for developing the electric field in the vicinity of the droplet, wherein the second electrode is fixed to the substrate, is insulated from the first electrode, and wherein the second electrode is located at about the center of the droplet; where the first electrode surrounds the second electrode.

3. The method of claim 2, wherein inward or outward radial electroosmotic flow of the particles inside the droplet is induced according to the characteristics of the particles.

* * * * *